United States Patent [19]

Van Bever

[11] 4,446,145

[45] May 1, 1984

[54] ANTI-MICROBIAL COMPOSITIONS FOR THE TOPICAL TREATMENT OF ACNE VULGARIS

[75] Inventor: Willem F. M. Van Bever, Turnhout, Belgium

[73] Assignee: Janssen Pharmaceutica N.V., Beerse, Belgium

[21] Appl. No.: 282,975

[22] Filed: Jul. 13, 1981

Related U.S. Application Data

[63] Continuation-in-part of Ser. No. 114,813, Jan. 24, 1980, abandoned.

[51] Int. Cl.$^3$ .............................................. A61K 31/415
[52] U.S. Cl. .................................. 424/273 R; 424/269; 424/338
[58] Field of Search .................... 424/273 R, 269, 338

[56] References Cited

U.S. PATENT DOCUMENTS 3,826,836  7/1974  Bochel et al. .................... 424/273
3,870,726  3/1975  Jager et al. ..................... 424/273 X
3,903,287  9/1975  Meiser et al. .................... 424/273

OTHER PUBLICATIONS

Hurwitz, Cutis, 17, 585–590 (1976).
Cunliffe et al, British Journal of Clinical Practice, Suppl. to 32 (8), 15 (1978).

Primary Examiner—Leonard Schenkman
Attorney, Agent, or Firm—Geoffrey G. Dellenbaugh

[57] ABSTRACT

Novel compositions for the topical treatment of acne vulgaris said compositions comprising a pharmaceutically acceptable amount of benzoylperoxide and an anti-microbially effective amount of a suitable azole derivative.

4 Claims, No Drawings

ANTI-MICROBIAL COMPOSITIONS FOR THE TOPICAL TREATMENT OF ACNE VULGARIS

CROSS-REFERENCE TO RELATED APPLICATIONS

This is a continuation-in-part of our copending application Ser. No. 114,813, filed Jan. 24, 1980 now abandoned.

BACKGROUND OF THE INVENTION

Compositions, which comprise benzoylperoxide as an active ingredient, are considered to be amongst the most effective ones in the treatment of acne vulgaris (see, for example, J. J. Leyden and A. M. Kligman, Drugs, 12, 292–300 (1976)). To improve the effect of benzoylperoxide there are frequently added to the compositions other known anti-acne substances. For example, as described by S. Hurwitz in Cutis 17, 585–590 (1976), there is a substantial increase in the therapeutic effect when benzoylperoxide is used in combination with retinoic acid. Considerable disadvantages of such compositions are, however, that they frequently cause allergic contact dermatitis and/or that they are, in certain cases, extremely irritating and drying, necessitating alteration of either the frequency or the duration of the applications or the concentration of the active ingredients in the composition.

Especially in the treatment of patients with inflammatory lesions, benzoylperoxide is often used in combination with orally administered antibiotics, e.g., tetracycline, erythromycine and the like. However, many questions have been raised concerning the safety of short- and long term use of orally administered antibiotics in the treatment of acne. Moreover, as a general rule, it is desirable to avoid oral therapy in the treatment of skin diseases whenever an effective topical treatment modality is available. Compositions, which are suitable for topical administration and which comprise benzoylperoxide in combination with, for example, erythromycine, are described in French Pat. No. 2,378,523. These compositions are known to reduce the numbers of Propionibacterium acnes, the main organism involved in the acne bearing areas.

W. J. Cunliffe and D. Gould, in British Journal of Clinical Practice, Suppl. to 32 (8), 15 (1978), described an experiment wherein a cream, containing 2% of micronazole nitrate, was tested in the treatment of acne. Although a positive effect was noted it was found that the numbers of *Propionibacterium acnes* and *Staphylococcus epidermidis* on the skin were not altered, despite the in vitro activity of micronazole against *Propionibacterium acnes*.

DESCRIPTION OF THE PREFERRED EMBODIMENTS

The present invention is concerned with pharmaceutical compositions for the topical treatment of acne vulgaris, which compositions are not irritating and have, compared with those known in the art, an improved anti-acne activity. These compositions comprise a pharmaceutically acceptable inert carrier material and as active ingredients mutually potentiating amounts of benzoylperoxide and of at least one chemical compound selected from the group consisting of an azole derivative having the formula

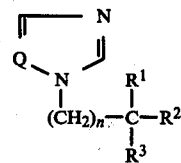

and the pharmaceutically acceptable acid addition salts thereof, wherein

Q is a member selected from the group consisting of CH and N;

n is 0 or the integer 1;

$R^1$ is a member selected from the group consisting of lower alkanoyl, hydroxylower alkyl, phenyl and phenyllower alkyl, wherein said phenyl radicals are optionally substituted with up to 3 halo atoms;

$R^2$ is a member selected from the group consisting of aryl, aryloxy, arylthio, aryllower alkyloxy and aryllower alkylthio, wherein said aryl is selected from the group consisting of phenyl, thienyl and halothienyl, said phenyl being optionally substituted with up to 3 halo atoms; and $R^3$ is a member selected from the group consisting of hydrogen, lower alkynyl, lower alkyloxycarbonyl and phenyl, said phenyl being optionally substituted with up to 3 substituents, each independently selected from the group consisting of halo and trifluoromethyl.

In the foregoing definitions the term halo is generic to fluoro, chloro, bromo and iodo; the term "lower alkyl" is meant to include straight and branch chained hydrocarbon radicals having from 1 to 6 carbon atoms such as, for example, methyl, ethyl, 1-methylethyl, 1,1-dimethylethyl, propyl, 2-methylpropyl, butyl, pentyl, hexyl and the like; and the term "lower alkynyl" refers to straight alkynyl radicals having from 2 to 6 carbon atoms such as, for example, ethynyl, 2-propynyl, 2-butynyl, 3-pentynyl, 2-hexynyl and the like.

Specific examples of azole derivatives within the scope of formule (I) are the followings:

1-[2-(2,4-dichlorophenyl)-2-[(2,6-dichlorophenyl)methoxy]ethyl]-1H-imidazole, generically designated as isoconazole;

1-[2-(2,4-dichlorophenyl)-2-[(2,4-dichlorophenyl)methoxy]ethyl]-1H-imidazole, generically designated as miconazole;

1-[2-(2,4-dichlorophenyl)-2-[(4-chlorophenyl)methoxy]ethyl]-1H-imidazole, generically designated as econazole;

1-[(2-chlorophenyl)diphenylmethyl]-1H-imidazole, generically designated as clotrimazole;

1-[2-(2,4-dichlorophenyl)-2-[(4-chlorophenyl)methylthio]ethyl]-1H-imidazole, generically designated as sulconazole;

1-(4-chlorophenoxy)-1-(1H-imidazol-1-yl)-3,3-dimethylbutan-2-one, generically designated as climbazole;

1-[2-(2,4-dichlorophenyl)-2-(2-thienylmethoxy)ethyl]-1H-imidazole;

1-[2-(4-chlorophenyl)-2-[(2,6-dichlorophenyl)methoxy]ethyl]-1H-imidazole, generically designated as orconazole;

1-[4-(4-chlorophenyl)-2-[(2,6-dichlorophenyl)thio]butyl]-1H-imidazole, generically designated as butoconazole;

1-(4-chlorophenoxy)-3,3-dimethyl-1-(1H-1,2,4-triazol-1-yl)-2-butanol, generically designated as triadimenol;

2-(4-chlorophenoxy)-4,4-dimethyl-1-(1H-1,2,4-triazol-1-yl)-3-pentanone;

1-[2-[(2-chloro-3-thienyl)methoxy]-2-(2,4-dichlorophenyl)ethyl]-1H-imidazole, generically designated as tioconazole;

2-(2,4-dichlorophenoxy)-1-(1H-imidazol-1-yl)-4,4-dimethylpentan-3-one, generically designated as valconazole;

1-(1,1-diphenyl-2-propynyl)-1H-imidazole; methyl α,α-diphenyl-1H-imidazole-1-acetate; and 1-[diphenyl[3-(trifluoromethyl)phenyl]methyl]-1H-1,2,4-triazole, generically designated as fluotrimazole.

Preferred compositions according to the present invention are those wherein the azole derivative is a compound of formula (I) wherein Q is CH.

Particularly preferred compositions are those wherein the azole derivative is selected from the group consisting of clotrimazole and a compound of formula (I) wherein Q is CH, n is 1, $R^1$ is mono- or dihalophenyl, $R^2$ is (mono- or dihalophenyl)methoxy and $R^3$ is hydrogen.

Especially preferred compositions are those wherein the azole derivative is selected from the group consisting of isoconazole, miconazole, econazole, clotrimazole and the pharmaceutically acceptable acid addition salts thereof.

More especially preferred compositions are those wherein the azole derivative is selected from the group consisting of miconazole and econazole and the pharmaceutically acceptable acid addition salts thereof.

The most preferred compositions according to the present invention are those wherein the azole derivative is selected from the group consisting of miconazole and the pharmaceutically acceptable acid addition salts thereof.

The azole derivatives used as active ingredients in the aforementioned compositions are known per se. Such compounds and their preparations have been described, for example, in U.S. Pat. Nos. 4,055,652; 4,062,966; 4,078,071; 3,974,174; 3,940,413; 3,657,445; 3,870,726; 3,826,836; 3,682,950; 3,723,622; 3,812,142; 3,903,287; 3,952,002; 3,717,655 and in Belgian Pat. No. 849,012.

The compounds of formula (I) may be converted to their therapeutically active non-toxic acid addition salt form by treatment with an appropriate acid, such as, for example, an inorganic acid, such as hydrohalic acid, e.g., hydrochloric, hydrobromic and the like, and sulfuric acid, nitric acid, phosphoric acid and the like; or an organic acid, such as, for example, acetic, propanoic, 2-hydroxyacetic, 2-hydroxypropanoic, 2-oxopropanoic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, benzoic, 3-phenyl-2-propenoic, α-hydroxybenzeneacetic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The efficacy and the mutually potentiating effect of the compositions comprised within the scope of the present invention are clearly demonstrated by their in vitro activities on *Staphylococcus epidermidis* B 2689 and B 180, and *Propionibacterium acnes* B 22, 267, which microorganisms may all be recovered from the skinlesions caused by acne vulgaris.

In vitro experiments

A. Materials and methods

1. Media

Tryptose broth contains 20 g of tryptose (Difco), 5 g of sodium chloride and 1 g of glucose per liter distilled water. Tryptose agar contains in addition 15 g agar.

2. Strains and inocula

Staphylococcus species are maintained on agar slants and subcultured twice on tryptose broth for 24 hours at 37° C. A loopful is inoculated in 4.5 ml of the same medium and grown at 37° C. for 64 hours. A 0.2 ml aliquot of the culture is used to inoculate 100 ml tryptose broth and cells are grown aerobically for 24 hours at 37° C. by shaking in a reciprocating shaker. A 0.20 ml sample, containing $1.10^9$ cells are used to inoculate 100 ml of tryptose broth whereto solvent and the investigated azole derivative and/or benzoylperoxide are added.

*Propionibacterium acnes* B 22,267, maintained on fluid thioglycollate medium, are subcultured for 72 h. at 37° C.; 0.2 ml aliquots of 48 h.-cultures (containing $5.0 \times 10^7$ cells/ml) are used to inoculate 15 ml of the experimental fluid thioglycollate medium.

3. Growth studies

Staphylococcus species cells are grown at 37° C. aerobically by shaking in a reciprocating shaker. The investigated azole derivative and/or benzoylperoxide are dissolved in dimethylsulfoxide and added to the media immediately before inoculation. Only freshly prepared benzoylperoxide solutions are used. Controls are similarly set up with equivalent quantities of dimethylsulfoxide (final concentration: 0.15%). *Propionibacterium acnes* B 22,267: drugs and/or solvent are also added just before inoculation. To remove oxygen from the medium, the inoculated fluid thioglycollate medium is flushed for 30 min. with oxygen-free sterile nitrogen.

4. Total count method

Samples of 0.1 ml are withdrawn from the cultures and diluted in Isoton ® (Coulter Electronics) containing 1% of formaldehyde. Cells are counted by means of a Coulter counter ®, model ZBI-biological (Coulter Electronics).

5. Viable count method

Samples are withdrawn from the cultures at different time intervals and decimally diluted in sterile 0.85% saline. Aliquots of 0.1 ml from the undiluted and diluted suspensions are plated on each of 4 replicate tryptoseagar plates. They are then incubated aerobically for 72 h. at 37° C. and the colonies are counted.

B. Results

Table 1 and table 2 show the inhibition caused by azole derivatives, alone and in combination with benzoylperoxide, on the growth of *Staphylococcus epidermidis* B 2689. Cells are grown on a tryptose broth medium; after 24 hours, samples are withdrawn from the cultures and counted. Results are presented in percentage of total number of cells in control cultures±standard deviation.

TABLE 1

Effect of azole derivatives alone and in combination with benzoylperoxide on growth of Staphylococcus epidermidis B 2689. The effect of benzoylperoxide (15 μg/ml) as percentage of control is 70.9 ± 25.1

| Concentration azole M | benzoylperoxide | miconazole | econazole | isoconazole | clotrimazole |
|---|---|---|---|---|---|
| $6 \times 10^{-8}$ | 0 | 96.8 | 99.9 | | |
| $6 \times 10^{-8}$ | 15 | 60.2 | 71.7 | | |
| $8 \times 10^{-8}$ | 0 | 95.6 ± 12.6 | 97.2 | | |
| $8 \times 10^{-8}$ | 15 | 36.0 ± 18.5 | 65.8 | | |
| $10^{-7}$ | 0 | 95.4 | 94.1 | 105.6 ± 2.5 | 105.7 |
| $10^{-7}$ | 15 | 39 | 55.7 | 100.6 ± 3.1 | 76.1 |
| $2 \times 10^{-7}$ | 0 | 93.4 | 95.1 | 104.0 ± 2.6 | 109.3 |
| $2 \times 10^{-7}$ | 15 | 39.7 | 55.8 | 85.9 ± 16.6 | 78.1 |
| $4 \times 10^{-7}$ | 0 | 73.3 ± 19.3 | 96.8 | 104.5 ± 3.3 | 103.2 |
| $4 \times 10^{-7}$ | 15 | 0.2 ± 0.1 | 58.4 | 0.21 ± 0.02 | 83.4 |
| $6 \times 10^{-7}$ | 0 | 87.3 | 91.6 | | 104.6 |
| $6 \times 10^{-7}$ | 15 | 0.02 | 31.6 | | 76.1 |
| $8 \times 10^{-7}$ | 0 | 86.8 | 92.2 | | 96.7 |
| $8 \times 10^{-7}$ | 15 | 0.04 | 0.07 | | 98.6 |
| $10^{-6}$ | 0 | 104.8 ± 9.4 | 79.3 ± 7.0 | 98.7 ± 8.1 | 87.2 ± 5.1 |
| $10^{-6}$ | 15 | 0.14 ± 0.05 | 0.4 ± 0.2 | 0.4 ± 0.2 | 18.4 ± 10.8 |
| $1.5 \times 10^{-6}$ | 0 | 84.4 ± 19.1 | 118.9 | | 95.8 |
| $1.5 \times 10^{-6}$ | 15 | 0.07 ± 0.03 | 0.16 | | |
| $2 \times 10^{-6}$ | 0 | 25.9 ± 1.6 | 107.1 | 95.3 ± 2.2 | 88.2 |
| $2 \times 10^{-6}$ | 15 | 0.08 ± 0.07 | 0.06 | 0.35 ± 0.12 | |
| $3 \times 10^{-6}$ | 0 | 0.08 | 70.9 | | 78.5 |
| $3 \times 10^{-6}$ | 15 | 0.06 | | | |
| $5 \times 10^{-6}$ | 0 | 0.06 | 1.00 | 0.32 ± 0.05 | 39.5 |
| $5 \times 10^{-6}$ | 15 | 0.05 | | | |
| $6 \times 10^{-6}$ | 0 | | | | 16.9 |
| $6 \times 10^{-6}$ | 15 | | | | 0.28 |
| $10^{-5}$ | 0 | | | 0.08 ± 0.01 | 2.0 |
| $10^{-5}$ | 15 | | | | 0.28 |

TABLE 2

Effect of miconazole alone and in combination with benzoylperoxide (BPO) on growth of Staphylococcus epidermidis B 180.

| Concentration miconazole M | BPO μg/ml | Percentage of control |
|---|---|---|
| 0 | 15 | 94.3 ± 5.5 |
| $8 \times 10^{-8}$ | 0 | 110.1 ± 6.3 |
| $8 \times 10^{-8}$ | 15 | 20.0 ± 24.4 |
| $10^{-7}$ | 0 | 105.2 ± 3.3 |
| $10^{-7}$ | 15 | 11.2 ± 18 |
| $2 \times 10^{-7}$ | 0 | 99.3 ± 2.2 |
| $2 \times 10^{-7}$ | 15 | 0.05 ± 0.01 |
| $4 \times 10^{-7}$ | 0 | 12.0 |
| $8 \times 10^{-7}$ | 0 | 11.0 |
| $10^{-6}$ | 0 | 15.9 |
| $2 \times 10^{-6}$ | 0 | 11.0 |
| $4 \times 10^{-6}$ | 0 | 0.25 |

Table 3 shows the effect of miconazole and/or benzoylperoxide on anaerobic growth of Propionibacterium acnes B 22,267. Miconazole and/or benzoylperoxide are added to the media immediately after inoculation; 24 h or 48 h later the total number (viable+non-viable) of cells is determined and expressed as percentage of the number of cells present in the media to which the solvent, dimethyl sulfoxide, is added. The results are the mean values of at least 2 experiments.

TABLE 3

Effect of miconazole and/or benzoylperoxide (BPO) on anaerobic growth of Propionibacterium acnes B 22,267.

| miconazole μg/ml | BPO μg/ml | 24 h. percentage of control | 48 h. percentage of control |
|---|---|---|---|
| — | 25 | 102.3 | 85.4 |
| — | 50 | 83.1 | 91.6 |

TABLE 3-continued

Effect of miconazole and/or benzoylperoxide (BPO) on anaerobic growth of Propionibacterium acnes B 22,267.

| miconazole μg/ml | BPO μg/ml | 24 h. percentage of control | 48 h. percentage of control |
|---|---|---|---|
| 3.0 | — | 29.1 | 72.7 |
| 3.0 | 25 | 3.0 | 16.2 |
| 3.0 | 50 | 2.8 | 14.6 |
| 4.0 | — | 20.3 | 55.4 |
| 4.0 | 25 | 2.0 | 2.7 |
| 4.0 | 50 | 3.6 | 4.8 |

Table 4 shows the effect of miconazole and/or benzoylperoxide on the viability of Staphylococcus epidermidis B 180 and B 2689. The samples are withdrawn from the cultures after 24 hours. The number of viable cells is determined as previously described herein. The results are represented as mean values±standard deviation.

TABLE 4

Effect of miconazole and/or benzoylperoxide (BPO) on the viability of Staphylococcus epidermidis B 180 and B 2689.

| Concentrations | | Percentage of control Staphylococcus epidermidis | |
|---|---|---|---|
| miconazole M | BPO μg/ml | B 180 | B 2689 |
| 0 | 15 | 47.5 ± 28.6 | 81.5 ± 18.8 |
| $8 \times 10^{-8}$ | 0 | | 104.0 ± 3.4 |
| $8 \times 10^{-8}$ | 15 | | 4.5 ± 5.8 |
| $10^{-7}$ | 0 | | 100.7 ± 17.8 |
| $10^{-7}$ | 15 | | 0.0 ± 0.0 |
| $2 \times 10^{-7}$ | 0 | | 66.0 ± 10.3 |
| $2 \times 10^{-7}$ | 15 | | 0.0 ± 0.0 |
| $10^{-6}$ | 0 | 78.5 ± 17.7 | |
| $10^{-6}$ | 15 | 0.0 ± 0.0 | |
| $2 \times 10^{-6}$ | 0 | 6.9 ± 1.7 | |

TABLE 4-continued

Effect of miconazole and/or benzoylperoxide (BPO) on the viability of Staphylococcus epidermidis B 180 and B 2689.

| Concentrations | | Percentage of control Staphylococcus epidermidis | |
|---|---|---|---|
| miconazole M | BPO µg/ml | B 180 | B 2689 |
| $2 \times 10^{-6}$ | 15 | $0.0 \pm 0.0$ | |

The efficacy and the mutually potentiating effect of the compositions comprised within the scope of the present invention are also demonstrated by the results of a double-blind clinical study which is described hereinafter. In this study the effectiveness of a composition comprising 5% of benzoylperoxide and 2% of miconazole is compared with that of the same composition without miconazole.

Double-blind clinical study

A total of 105 patients took part in the study. Table 5 gives the individual characteristics of the patients, including sex, age (median and extremes), the duration of the acne affection (in months) at the start of the study and the distribution of the patients in groups I and II as it appeared after the double-blind code was broken.

TABLE 5

| | group I n = 53 | group II n = 52 | total population n = 105 |
|---|---|---|---|
| sex - male | 30 | 26 | 56 |
| - female | 23 | 26 | 49 |
| age - median | 18 | 18 | 18 |
| - extremities | 13–24 | 12–24 | 12–24 |
| duration - median | 12 | 18 | 15 |
| - extremities | 4–120 | 3–72 | 3–120 |

All patients suffered from acne with a moderate to severe facial acne according to grades 1 or 2 of the following scale:

grade 0: the entire face is generally covered with very inflammed lesions. Pustules are also extended to the neck and under the chin:
grade 1: inflammation and pustules; most of the face is involved;
grade 2: slight but still clearly visible inflammation and swelling; in general pustules are absent;
grade 3: almost cured; lesions have practically disappeared; no inflammation or pustules;
grade 4: completely cured; no lesions or inflammation left; scars may still be visible in very severe cases.

The patients, which all had stopped previous treatment at least one week before the start of trial, were randomly given a coded medication that comprised either benzoylperoxide 5% (group I) or a combination of miconazole 2% with benzoylperoxide 5% (group II). The patients were instructed to apply the cream twice daily (morning and evening) and to avoid any other topical or oral treatment during trial. At the initial examination and 4, 8 and 12 weeks thereafter all patients were assessed according to the above mentioned 4-point acne grading scale. Furthermore, comedones were counted and patients were questioned about side-effects such as, for example, irritation of the skin.

TABLE 6 shows the shifts in the acne score according to the above mentioned 4-point acne grading scale after 4, 8 and 12 weeks in comparison with the status at the start of the treatment; n is the number of patients taken into consideration.

| | | shifts in score | | | | | | |
|---|---|---|---|---|---|---|---|---|
| | | −3 | −2 | −1 | 0 | +1 | +2 | +3 |
| week 4 vs. start | group I (n = 50) | — | — | 1 | 26 | 23 | — | — |
| | group II (n = 50) | — | — | 2 | 10 | 35 | 3 | — |
| week 8 vs. start | group I (n = 50) | — | — | 1 | 12 | 28 | 9 | — |
| | group II (n = 40) | — | — | — | 3 | 26 | 19 | 1 |
| week 12 vs. start | group I (n = 49) | — | — | 2 | 8 | 22 | 16 | 1 |
| | group II (n = 47) | — | — | — | 2 | 15 | 26 | 4 |
| | | deteriorated | | | | ameliorated | | |

TABLE 7 shows the median numbers of comedones at the start and after 4, 8 and 12 weeks of treatment; n is the number of patients taken into consideration.

| | median numbers of comedones | |
|---|---|---|
| | group I | group II |
| week 0 | 37 (n = 35) | 37 (n = 39) |
| week 4 | 22 (n = 32) | 17 (n = 38) |
| week 8 | 14 (n = 33) | 8 (n = 36) |
| week 12 | 11 (n = 32) | 3 (n = 35) |

At the final examination, 12 weeks after the start of the study, the opinion of the patients and the investigators concerning the evolution of the affection since the beginning of the treatment was registered as follows:
excellent: complete and rapid disappearance of signes and symptoms;
good: marked but less rapid improvement;
moderate: slight but definite improvement;
bad: no amelioration or deterioration.

TABLE 8 shows the scores which were given by the investigators and by the patients after 12 weeks of treatment; n is the number of patients taken into consideration.

| | According to investigators | | | According to patients | | |
|---|---|---|---|---|---|---|
| | group I | group II | group II versus group I | group I | group II | group II versus group I |
| excellent | 8 | 22 | | 10 | 28 | |
| good | 13 | 21 | p* | 17 | 17 | p* |
| moderate | 23 | 7 | <0.001 | 21 | 5 | <0.001 |
| bad | 7 | 1 | | 3 | 1 | |

*Mann - Whitney U test (two tailed probability)

In the group of patients who were treated with the combination of benzoylperoxide and miconazole (group II), there was a much lower frequence of irritation than in the benzoylperoxide group (group I). In fact only 1 patient of group II showed a moderate and transient irritation after 4 weeks of treatment while the same side effect occurred with 10 patients of group I.

In concluding it can be said that the compositions according to the present invention are highly effective against acne vulgaris. In fact in the above clinical trial a marked improvement was reached in not less than 88% of the patients treated with the combination of benzoylperoxide and miconazole while on third of the patients were completely cured at the end of the treatment, i.e. after 12 weeks.

It is evident from the double-blind clinical study and the in vitro experiments that the compositions containing benzoylperoxide in combination with an azole derivative are more effective than the compositions containing either benzoylperoxide or an azole derivative of formula (I) alone and, moreover, that the azole derivatives of formula (I) and benzoylperoxide, when combined together, have mutually potentiating activities.

For example, it is evidenced by the data in the tables 1, 2, 3 and 4 that the combination of benzoylperoxide and an azole derivative of formula (I) decrease the number and the viability of *Staphylococcus epidermidis* cells and *Propionibacterium acnes* cells in a larger measure than the sum of their respective effects, when benzoylperoxide and an azole derivative are administered separately. This mutually potentiating activity results in a decrease of the number of comedones in the skin of patients suffering from acne vulgaris when treated with a composition comprising benzoylperoxide and an azole derivative of formula (I), as shown in table 7.

Although the double-blind clinical study described the mutually potentiating effect only for compositions containing benzoylperoxide and miconazole it is evident from the in-vitro experiments that said mutual potentiation is also observed in the compositions wherein miconazole is interchanged by another azole derivative of formula (I) or an acid addition salt thereof. Preferably, the present invention provides compositions containing benzoylperoxide and at least one member selected from the group consisting of miconazole, econazole, isoconazole, clotrimazole and a pharmaceutically acceptable acid addition salt thereof.

Especially preferred compositions contain benzoylperoxide and at least one member selected from the group consisting of miconazole, econazole and a pharmaceutically acceptable acid addition salt thereof. Even more preferred compositions contain benzoylperoxide and miconazole or a pharmaceutically acceptable acid addition salt thereof.

As can be seen from the tables 1, 2, 3 and 4 the mutual potentiation of benzoylperoxide and an azole derivative of formula (I) occurs within a wide concentration range of both active ingredients. Since the mutual potentiation can easily be determined, it is evident for someone skilled in the art that the concentrations can be changed away from those used in the double-blind clinical study.

While the concentration range of the azole derivative is limited by a decrease and, finally, a complete absence of activity by lowering the concentration, the upper-limit of the concentration-range is defined by the solubility of the azole derivative or the acid addition salt thereof. Once this limit is exceeded, the activity of the composition is not increased although the concentration of the azole derivative is increased. Suitable concentrations of the azole derivatives are comprised between 0.25% and 5% and, preferably, the concentration is limited between 0.75% and 3%, and most preferably, between 1.5% and 2.5%.

The under-limit of the benzoylperoxide concentration-range is defined by a decrease and, finally, a complete absence of activity in the treatment of acne vulgaris. The upper-limit is defined by an increasing and, finally, unacceptable irritation and, consequently, suitable concentrations of benzoylperoxide are comprised between 0.5% and 12% and, preferably, the concentration is varying between 3% and 10% and, most preferably, the concentration is varying between 4 and 6%.

In comparison with the prior-art compositions containing benzoylperoxide the subject compositions have the advantage that comparable and even higher activities are obtained at lower concentrations of benzoylperoxide, thus avoiding undesirable skin irritations while simultaneously effectively treating the acne.

In view of the aforementioned anti-acne activity this invention provides a pharmaceutical anti-acne composition comprising a pharmaceutically acceptable inert carrier material and as active ingredients mutually potentiating amounts of benzoylperoxide and of at least one azole derivative having the formula (I) or a pharmaceutically acceptable acid addition salt thereof.

By the term "mutually potentiating" is meant that the azole derivative and the benzoylperoxide in the subject compositions exert a greater activity in combination than the sum of their individual activities when used separately.

The term "composition" comprises valuable creams, ointments and lotions.

These compositions should preferably be non-irritating and as far as possible they should be odorless and non-toxic. For convenience in applying to the skin, the compositions usually contain, besides from about 40 to about 90% of water or an organic solvent, several of certain organic emollients, emulsifiers for the aqueous and/or the non aqueous phases of the compositions, wetting agents, preservatives and anti-oxidants. Solvents which are suitable for this purpose are high-boiling oils such as, for example, vegetable oils, lower-boiling solvents with a flash point of at least 30° C. and the like. It is, of course, also possible to use mixtures of solvents. Suitable organic emollients are, for example, aliphatic alcohols having from 4 to 20 carbon atoms and glycols having from 2 to 3 carbon atoms, polymers of these glycols, fatty acids having from 12 to 20 carbon atoms and the esters of the said acids. Emulsifiers, which may be used, are, for example, polyethylene glycol 1000 monostearate, polyoxyethylene sorbitan monooleate, e.g., tween 20, and the like. Useful preservatives are methylparaben, propylparaben and the like, while butylated hydroxytoluols and hydroxyanisols may be used as anti-oxidants.

Lotions can be made in the usual way for making solutions, i.e., by stirring the constituents together, if necessary, with assistance of solution promotors.

Ointments and creams may be prepared by carefully and thoroughly blending the benzoylperoxide, organic emollients, water and other constituents of the composition. Advantageously, the fluid medium in which the benzoylperoxide is to be dispersed is first prepared by forming an emulsion of the aqueous and non-aqueous phases and, subsequently, benzoylperoxide and an azole derivative of formula (I) or a pharmaceutically acceptable acid-addition salt thereof is added to the emulsion and thoroughly blended with it.

The following examples are representative but not limitative of the therapeutic compositions prepared in accordance with the present invention.

EXAMPLE I

1. The aqueous emulsion

At room temperature 75.0 g tween and 8.960 liters purified water are added to 3600.0 g. benzoylperoxide paste (benzoylperoxide: 70%), which is passed through a 2.9 mm. sieve. 1000 g miconazole nitrate is added and the whole is mixed until complete wetting. The thus obtained suspension is homogenized to break all agglomerations.

2. The non-aqueous emulsion

A warm (60°-70° C.) mixture of 5000.0 g. propylene glycol and 800.0 g. sodium laurylsulfate is added to a molten mixture of 6000.0 g. cetyl alcohol and 500.0 g. white wax.

3. The preparation of the final composition

The aqueous emulsion is added slowly to the non-aqueous emulsion of 30°±2° C. and the whole is mixed to homogeneous for about 30 minutes and diluted with water to a total volume of 50 liters.

EXAMPLE II

1. The aqueous emulsion

A solution of 0.600 kg. benzoic acid in 210 liters purified water is added at 65°±5° C. to a mixture consisting of 12.825 kg. molten tefose 63, 4.285 l. labrafil M 1944 CS, 21 kg. mineral oil and 9.600 kg. butylated hydroxyanisole.

2. The non-aqueous emulsion 6 kg. miconazole nitrate is added to a suspension of 0.675 kg. tefose 63 and 8.5 kg. benzoylperoxide paste (benzoylperoxide: 70%) in 36.350 l. purified water (25°±5° C.), while vigorous stirring until the miconazole nitrate is well wetted. The thus obtained emulsion is homogenized.

3. The preparation of the final composition

The aqueous emulsion is added slowly to the non-aqueous emulsion. While mixing is continued the thus obtained lotion is cooled to 7°-8° C.

What is claimed is:

1. A pharmaceutical anti-acne composition comprising a pharmaceutically acceptable inert carrier material and as active ingredients from 4% to 6% of benzoylperoxide and from 1.5% to 2.5% of at least one chemical compound selected from the group consisting of clotrimazole, miconazole, econazole, isoconazole and a pharmaceutically acceptable acid addition salt thereof.

2. A pharmaceutical anti-acne composition comprising a pharmaceutically acceptable inert carrier material and as active ingredient from 4% to 6% of benzoylperoxide and from 1.5% to 2.5% of a chemical compound selected from the group consisting of miconazole, econazole and a pharmaceutically acceptable acid addition salt thereof.

3. A pharmaceutical anti-acne composition comprising a pharmaceutically acceptable inert carrier material and as active ingredients from 4% to 6% of benzoylperoxide and from 1.5% to 2.5% of a chemical compound selected from the group consisting of miconazole and a pharmaceutically acceptable acid addition salt thereof.

4. A pharmaceutical anti-acne composition comprising a pharmaceutically acceptable inert carrier material and as active ingredient about 5% of benzoylperoxide and about 2% of a chemical compound selected from the group consisting of miconazole and a pharmaceutically acceptable acid addition salt thereof.

* * * * *